United States Patent
Monte

[11] Patent Number: 5,810,018
[45] Date of Patent: Sep. 22, 1998

[54] METHOD, COMPOSITION AND APPARATUS FOR REDUCING THE INCIDENCE OF CIGARETTE SMOKING

[76] Inventor: Woodrow C. Monte, 6411 S. River Dr., #65, Tempe, Ariz. 85283

[21] Appl. No.: 365,768

[22] Filed: Dec. 29, 1994

[51] Int. Cl.⁶ .................................................. A24F 47/00
[52] U.S. Cl. ............................ 131/270; 131/271; 514/81.3
[58] Field of Search ..................... 131/270, 271; 514/81.3

[56] References Cited

U.S. PATENT DOCUMENTS

| | | | |
|---|---|---|---|
| 3,757,798 | 9/1973 | Lambert | 131/270 |
| 4,778,677 | 10/1988 | Ebbesen | 514/813 X |
| 4,953,572 | 9/1990 | Rose et al. | 131/270 |
| 5,051,426 | 9/1991 | Parnell | 514/813 X |

OTHER PUBLICATIONS

*The Condensed Chemical Dictionary*, Hawley, p. 915, 4–1983.

*Tobacco Flavoring For Smoking Products*, Leffingwell et al., pp. 3–8, 10, 11 and 14, 1972.

Primary Examiner—Vincent Millin
Assistant Examiner—William J. Deane, Jr.
Attorney, Agent, or Firm—Tod R. Nissle, P.C.

[57] ABSTRACT

Effective concentrations of nicotine, of a stimulant, and of a sequestering agent are admixed in a liquid carrier. The sequestering agent prevents binding of nicotine with metallic ions which interfere with absorption of nicotine through the lining of the oral cavity. The liquid solution is sprayed into the oral cavity for simultaneous absorption of the nicotine and stimulant through the lining of the oral cavity.

5 Claims, 1 Drawing Sheet

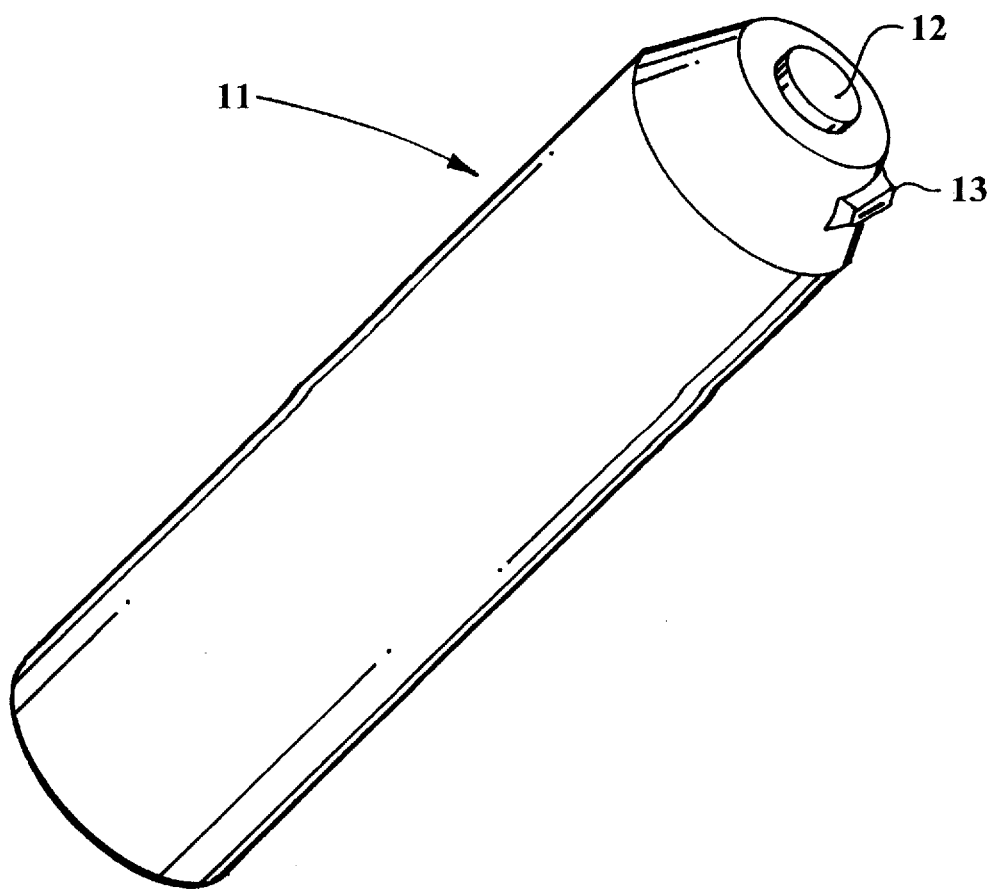

METHOD, COMPOSITION AND APPARATUS FOR REDUCING THE INCIDENCE OF CIGARETTE SMOKING

This invention relates to an apparatus, composition, and method for reducing the incidence of tobacco smoking.

More particularly, the invention relates to an apparatus, composition, and method which facilitate the absorption of nicotine through the linings of the mouth in order to reduce the incidence of tobacco smoking.

Nicotine is an addictive poisonous alkaloid $C_5H_4NC_4H_7NCH_3$, derived from the tobacco plant. Nicotine is used as an insecticide. Forty milligrams of nicotine has killed an adult (Merck Index). One deep drag on a cigarette can provide 0.35 mg nicotine. Therefore, one cigarette can provide 3.5 mg of nicotine and twenty one cigarettes provide 73.5 mg of nicotine. There is often in excess 250 mg of nicotine in one hundred cigarettes. pp. 375 and 379, Wynder, E. L. and Hoffman, D, *Tobacco and Tobacco Smoke. Studies in Experimental Carcinogenesis.* (1967); Academic Press, New York. When smoking a cigarette, nicotine is quickly absorbed into the smoker's blood and reaches the brain within eight seconds after inhalation. The poisonous, toxic, carcinogenic, and addictive nature of nicotine has provided impetus for methods, compositions, and apparatus which help break the dependency of individuals on cigarettes.

U.S. Pat. No. 4,63,651 to Jacobs describes an inhalable aerosol spray. The aerosol spray includes small particles charged with nicotine. The particles are carried into the lungs of the user. A disadvantage of this spray is that the inhalation of particulate matter can be unadvisable, particularly for individuals suffering from asthma or other lung diseases.

U.S. Pat. No. 3,439,685 to Allen discloses a method for reducing cigarette smoking in which a smoker is provided with a series of cigarettes in which the amount of nicotine is gradually reduced and the amount of a bitter tasting substance is gradually increased. A problem with utilizing the cigarettes proposed by Allen is that smokers will, because of the bitter tasting substance, simply refuse to smoke Allen's cigarettes and will return to conventional cigarettes which do not produce a bitter taste.

U.S. Pat. No. 4,715,387 to Rose discloses an oral spray which includes particles of a food acid which can be inhaled. The food acid simulates the sensation in the respiratory tract normally caused by tobacco smoke. The oral spray can be utilized in conjunction with transdermally applied nicotine. The inhalation of particulate matter into the respiratory tract of an individual can, as noted above, be undesirable for individuals suffering from asthma or other respiratory diseases.

U.S. Pat. No. 4,747,417 to Beskin discloses an oral spray which, when applied to the mouth, reacts with nicotine to produce an unpleasant metallic taste which discourages smoking. The spray includes silver acetate. The Beskin oral spray suffers from the same disadvantage as the Allen cigarettes, namely the cigarette and cigar smokers will simply refuse to use the bitter tasting spray and will return to the use of conventional tobacco products which do not produce an unpleasant taste.

Accordingly, it would be highly desirable to provide a method, composition, and apparatus which facilitates lowering the incidence of tobacco smoking without producing a bitter taste in the mouth of an individual and without requiring that the individual inhale particulate.

It would also be highly desirable to provide a method, composition, and apparatus which lowers the incidence of tobacco smoking and which does not rely on the absorption of nicotine through the alveoli in the lungs of an individual.

Therefore, it is a principal object of the invention to provide an improved method, composition and apparatus for helping an individual end his addiction to nicotine and to smoking tobacco products which are a source of nicotine.

A further object of the invention is to provide an improved method, composition and apparatus for facilitating the lowering of incidence of tobacco smoking without relying on the production of a bitter taste in the mouth of an individual and without relying on the introduction of particulate in the lungs of an individual.

Another object of the invention is to provide a method, composition and apparatus which negates individual's reliance on tobacco smoking without requiring the introduction of compositions through the epidermis or lungs of the individual.

These and other, further and more specific objects and advantages of the invention will be apparent to those skilled in the art from the following detailed description thereof, taken in conjunction with the drawing, which depicts a spray container constructed in accordance with the principles of the invention.

Briefly, in accordance with my invention, I provide an improved method of aiding in the reduction of incidence of tobacco smoking. The method includes the step of sequentially administering for selected periods of time to the oral cavity of an individual a sequence of sprays each containing progressively lower concentrations of nicotine and progressively greater concentrations of a selected stimulant. The nicotine and stimulant in the spray are each substantially absorbed into the individual's body through the linings of the oral cavity.

In another embodiment of the invention, I provide improved apparatus for aiding in the reduction of the incidence of tobacco smoking. The apparatus includes a first spray container carrying a solution having for absorption into the individual's body through the linings of the individual's oral cavity a selected concentration of nicotine and a selected concentration of a stimulant other than nicotine; and, at least one other spray container carrying a solution having for absorption into the individual's body through the linings of the individual's oral cavity a selected concentration of nicotine less than the selected concentration in the first spray container and, a selected concentration of a stimulant greater than the selected concentration in the second spray container. The first spray container is utilized by the individual for a selected period of time to administer sprays to the oral cavity of the individual, after which the second spray container is utilized for a selected period of time to administer sprays to the oral cavity of the individual.

In a further embodiment of the invention, I provide improved apparatus for aiding in the reduction of the incidence of tobacco smoking. The apparatus includes a first spray container carrying a solution. The solution includes a sequestering agent which binds with metallic ions and with acids, and includes for absorption into the individual's body through the linings of the individual's oral cavity a selected concentration of nicotine and a selected concentration of a stimulant other than nicotine. The apparatus also includes at least one other spray container carrying a solution. The solution in the other spray container includes for absorption into the individual's body through the linings of the individual's oral cavity a selected concentration of nicotine less than the selected concentration in the first spray container; includes a selected concentration of a stimulant greater than the selected concentration in the second spray container;

and, includes a sequestering agent which binds with metallic ions and with acids. The first spray container is utilized by the individual for a selected period of time to administer sprays to the oral cavity of the individual, after which the second spray container is utilized for a selected period of time to administer sprays to the oral cavity of the individual.

In still another embodiment of the invention, I provide a composition for facilitating the absorption of nicotine through the linings of the oral cavity of an individual. The composition comprises a liquid carrier; less than 2% by weight nicotine; less than 10% by weight of a stimulant; and, less than 250 ppm of a sequestering agent which binds with metallic ions and with acids.

Turning now to the drawing, which depicts a presently preferred embodiment of the apparatus of the invention for the purpose of illustrating the practice thereof and not by way of limitation of the scope of the invention, FIG. 1 illustrates a spray container used in the practice of the invention. The spray container 11 presently holds up to one hundred milliliters of fluid and can be sequentially filled or charged with a sequence of nicotine—stimulant liquid solutions of differing composition, or, a plurality of identical or similar spray containers can be utilized, each container being filled with a nicotine—stimulant liquid solution of differing composition. As will be described below, the nicotine—stimulant liquid solution can, if desired, not contain nicotine or a stimulant. Spray container 11 can be a conventional pressurized aerosol container that emits a mist or spray through nozzle 13 when valve-control button 13 is manually depressed; can be a conventional pump-type liquid container which pumps fluid from the container out through nozzle 13 as a spray due to motive force generated when button 13 is manually depressed; or, can be any other type of container which in use emits a spray or mist through a nozzle 13. Container 11 is presently preferably shaped and dimensioned to be concealed on the person or in a purse and preferably is a self-contained manually actuated or operated container. In one embodiment of the invention a pump-type container is preferred because pump-type containers usually include a nozzle which can be unscrewed from the body of the container such that the fluid in the container can be readily discarded and replaced by new fluid, after which the nozzle is screwed back onto the body of the container. In contrast, many aerosol containers are sealed shut and do not permit the ready replacement of fluid in the containers. Since the spray produced by container 11 is not intended to be inhaled, the spray emitted from nozzle 13 need not be a mist, but can be a coarser spray which wets and remains in the mouth of the user.

Each liquid solution used in a spray container 11 includes a selected amount of nicotine, of a stimulant, and/or of a sequestering agent. The amount of nicotine utilized in the each liquid solution is presently less than 2% by weight, preferably less than about 1% by weight. The amount of the stimulant utilized in the liquid composition is less than 10% by weight, preferably less than about 5% by weight. The amount of sequestering agent utilize in the liquid solution is less than 250 parts per million (ppm) preferably less than about 150 ppm.

The spray container 11 is used to direct a spray solution into the oral cavity of an individual such that nicotine is immediately absorbed into the individual's body through the lining of the mouth. It is believed that the absorption of nicotine through the lining of the mouth is hindered because nicotine combines with metallic ions to form salts which are not readily absorbed through the mucous linings of the mouth. Accordingly, in preparing liquid solutions containing nicotine in accordance with the invention, a sequestering agent such as EDTA is incorporated into the liquid solution to reduce the combination of nicotine with acids and metallic ions. The sequestering agent combines with acids and metallic ions to prevent the bonding or attachment of nicotine to the acids and metallic ions to form salts. The sequestering agent also preferably does not combine with or alter the structure of nicotine in such a way to reduce the ability of nicotine to be absorbed through the mucous linings of the mouth.

While scopolamine or any other alkaloid or stimulant can be utilized in the practice of the invention, caffeine is presently preferred because it is often less likely than other alkaloids or stimulants to become habit forming.

The liquid carrier in the spray solution is water, alcohol, or any other desired liquid. The liquid carrier is, however, typically an aqueous solution. When caffeine is the stimulant utilized in conjunction with nicotine, the liquid carrier is preferably an alcohol—water mixture because caffeine is at its maximum solubility in such a mixture. The sequence of solutions preferred in the use of the invention gradually decreases the amount of nicotine in each solution and increases the amount of caffeine. Eventually, a solution is used which contains only caffeine and does not contain nicotine. Solutions which contain only caffeine and do not contain nicotine do not include a sequestering agent and also preferably include ascorbic acid which improves the solubility of the caffeine. The amount, by weight, of ascorbic acid used is preferably over twice the amount, by weight, of caffeine present in the liquid solution.

The following examples are presented by way of demonstration, and not limitation, of the invention.

EXAMPLE 1

Two liters of a stock nicotine solution were prepared by mixing together the following components:
Water 800.0 grams
Saccharine Na 20.0 grams
Disodium EDTA (100 ppm) 0.2 gram
Ethanol 960.0 grams
Nicotine (Free Base) 10.0 grams
Oil of Peppermint q.s.

EXAMPLE 2

Two liters of a stock caffeine solution were prepared by mixing together the following components:
Water 800.00 grams
Saccharine Na 20.00 grams
Disodium EDTA (100 ppm) 0.20 gram
Ethanol (peppermint) 920.00 grams
Caffeine (Free Base) 36.36 grams

EXAMPLE 3

Two liters of a stock caffeine solution were prepared by mixing together the following components:
Water 800.00 grams
Saccharine Na 20.00 grams
Ethanol 920.00 grams
Caffeine (Free Base) 86.40 grams

EXAMPLE 4

A first spray solution was prepared by taking 80 milliliters (ml) of the stock solution of Example 1.

EXAMPLE 5

A second spray solution was prepared by mixing sixty-four (64) ml of the stock solution of Example 1 with sixteen (16) ml of the stock solution of Example 2.

EXAMPLE 6

A third spray solution was prepared by mixing forty-eight (48) ml of the stock solution of Example 1 with thirty-two (32) ml of the stock solution of Example 2.

EXAMPLE 7

A fourth spray solution was prepared by mixing thirty-two (32) ml of the stock solution of Example 1 with forty-eight (48) ml of the stock solution of Example 2.

EXAMPLE 8

A fifth spray solution was prepared by mixing sixteen (16) ml of the stock solution of Example 1 with sixty-four (64) ml of the stock solution of Example 2.

EXAMPLE 9

A sixth spray solution was prepared by mixing eight (8) ml of the stock solution of Example 1 with seventy-two (72) ml of the stock solution of Example 2.

EXAMPLE 10

A seventh spray solution was prepared by taking eighty ml of the stock solution of Example 2.

EXAMPLE 11

A subject Caucasian male with an age in his late thirties underwent the seven week treatment described below. Prior to the seven week treatment, the subject caucasian male smoked at least one pack of cigarettes a day and smokes cigars. During the seven week treatment, the subject did not smoke cigarettes or cigars.

The first spray solution of Example 4 was loaded into the spray container 11 and was used for a seven day period (Week #1) in place of cigarettes and cigars by the subject. Whenever the subject desired a cigarette or cigar during Week #1, he sprayed fluid from container 11 into his mouth.

For the next seven day period (Week #2) immediately following Week #1, the container 11 was emptied, and the second spray solution of Example 5 was loaded into the spray container 11 and was used by the subject in place of cigarettes and cigars. Whenever the subject desired a cigarette or cigar during Week #2, he sprays fluid from container 11 into his mouth.

For the next seven day period (Week #3) immediately following Week #2, the container 11 was emptied, and the third spray solution of Example 6 was loaded into the spray container 11 and was used by the subject in place of cigarettes and cigars. Whenever the subject desired a cigarette or cigar during Week #3, he sprayed fluid from container 11 into his mouth.

For the next seven day period (Week #4) immediately following Week #3, the container 11 was emptied, and the fourth spray solution of Example 7 was loaded into the spray container 11 and was used by the subject in place of cigarettes and cigars. Whenever the subject desired a cigarette or cigar during Week #4, he sprayed fluid from container 11 into his mouth.

For the next seven day period (Week #5) immediately following Week #4, the container 11 was emptied, and the fifth spray solution of Example 8 was loaded into the spray container 11 and was used by the subject in place of cigarettes and cigars. Whenever the subject desired a cigarette or cigar during Week #5, he sprayed fluid from container 11 into his mouth.

For the next seven day period (Week #6) immediately following Week #5, the container 11 was emptied, and the sixth spray solution of Example 9 was loaded into the spray container 11 and was used by the subject in place of cigarettes or cigars. Whenever the subject desires a cigarette or cigar during Week #6, he sprayed fluid from container 11 into his mouth.

For the next seven day period (Week #7) immediately following Week #6, the container 11 was emptied, and the seventh spray solution of Example 10 was loaded into the spray container 11 and was used by the subject in place of cigarettes or cigars. Whenever the subject desired a cigarette or cigar during Week #7, he sprayed fluid from container 11 into his mouth.

After Week #7, the subject ceased use of container 11 and of nicotine—caffeine spray solutions. During the two years following Week #7, the subject did not smoke cigarettes or cigars or use any tobacco products or use products which contained nicotine.

If desired, instead of continually emptying and recharging container 11 in the manner described in this Example 11, seven separate containers, each holding a different one of the seven spray solutions, could be utilized. Further, the number of spray solutions can be varied as desired. Instead of utilizing seven solutions in which the amount of nicotine decreases and the amount of caffeine increases in the manner described in Examples 4 to 10, six or fewer of such solutions may be utilized. Or, eight or more spray solutions may be utilized.

EXAMPLE 12

Example 11 is repeated except that the subject is a twenty year old caucasian woman who smokes one pack of cigarettes a day. Similar results are obtained.

EXAMPLE 13

Example 11 is repeated except that the subject is a fifty-two year old black male who smokes one pack of cigarettes a day. Similar results are obtained.

EXAMPLE 14

Examples 1 and 2 and 4 to 11 are repeated except that the nicotine spray solution of Example 1 contains six grams of nicotine instead of ten grams. Similar results are obtained.

EXAMPLE 15

Examples 1 and 2 and 4 to 11 are repeated except that the caffeine spray solution of Example 2 contains twenty grams of caffeine instead of 36.36 grams. Similar results are obtained.

EXAMPLE 16

Examples 1 and 2 and 4 to 11 are repeated except that the nicotine spray solution of Example 1 contains fifty ppm EDTA instead of one hundred ppm. Similar results are obtained.

EXAMPLE 17

Examples 1 and 2 and 4 to 11 are repeated except that the caffeine spray solution of Example 2 contains fifty ppm EDTA instead of one hundred ppm. Similar results are obtained.

EXAMPLE 18

Examples 1 and 2 and 4 to 11 are repeated except that the nicotine spray solution of Example 1 contains sixteen grams of nicotine instead of ten grams. Similar results are obtained.

EXAMPLE 19

Examples 1 and 2 and 4 to 11 are repeated except that the caffeine spray solution of Example 2 contains fifty-two grams of caffeine instead of 36.36 grams. Similar results are obtained.

EXAMPLE 20

Examples 1 and 2 and 4 to 11 are repeated except that the nicotine spray solution of Example 1 contains two hundred ppm EDTA instead of one hundred ppm. Similar results are obtained.

EXAMPLE 21

Examples 1 and 2 and 4 to 11 are repeated except that the caffeine spray solution of Example 2 contains two hundred ppm EDTA instead of one hundred ppm. Similar results are obtained.

EXAMPLE 22

Example 11 is repeated except each spray solution is used for a period of three days instead of seven days. Similar results are obtained.

EXAMPLE 23

Example 11 is repeated except each spray solution is used for a period of fourteen days instead of seven days. Similar results are obtained. As indicated by Examples 22 and 23, the period of time each spray solution is utilized can be varied as desired, as can the frequency of use of each spray solution.

EXAMPLE 24

Example 11 is repeated except that the third and fourth spray solutions are not utilized. Similar results are obtained.

EXAMPLE 25

Example 11 is repeated except that the first, second, third, fourth, and fifth spray solutions are not utilized, and the sixth and seventh spray solutions are each utilized for three weeks instead of one week. Similar results are obtained.

Having described my invention in such terms as to enable those skilled in the art to understand and practice it, I claim:

1. A method of aiding in the reduction of incidence of tobacco smoking, said method comprising the steps of:
    (a) providing at least one spray container;
    (b) providing a plurality of liquid carrier solutions, each of said liquid carrier solutions containing
        (i) progressively lower concentrations of nicotine and progressively greater concentrations of at least one selected stimulant, and
        (ii) a liquid carrier, quantities of nicotine and of the selected stimulant being admixed with said liquid carrier to form said liquid carrier solution;
        (iii) a sequestering agent to reduce the combination of nicotine with metallic ions and acids and to promote the absorption of nicotine through the lining of the oral cavity of the individual; and,
    (c) administering to the oral cavity of an individual each of said plurality of sprays during only one of a plurality of sequential selected periods of time to incrementally
        (i) decrease the concentration of nicotine provided, and
        (ii) increase the concentration of stimulant provided,
    each of said sprays being administered separately in said spray container during a different one of said selected periods of time, and
    nicotine and stimulant in each of said sprays being absorbed into the individual's body through the linings of the oral cavity.

2. The method of claim 1 wherein in step (b) each of said liquid carrier solutions includes
    (a) less than 2% by weight nicotine;
    (b) less than 10% by weight of at least one stimulant; and,
    (c) less than 250 ppm of a sequestering agent which binds with metallic ions and acids.

3. Apparatus for aiding in the reduction of the incidence of tobacco smoking, including
    (a) a first spray container carrying a first liquid carrier solution, said carrier solution having for absorption into the individual's body through the lining of the individual's oral cavity a selected concentration of nicotine and a selected concentration of a stimulant other than nicotine, said nicotine and said stimulant being admixed together in a liquid carrier to form said liquid carrier solution; and,
    (b) at least one other spray container carrying a second liquid carrier solution, said second carrier solution having for absorption into the individual's body through the linings of the individual's oral cavity
        (i) a selected concentration of nicotine less than the selected concentration of nicotine in said first liquid carrier solution, and
        (ii) a selected concentration of at least one stimulant greater than said selected concentration of stimulant in said first liquid carrier solution,
    said nicotine and said stimulant in said second liquid carrier solution being admixed together in a liquid carrier to form said second liquid carrier solution,
    said first and second liquid carrier solutions each including a sequestering agent to reduce the combination of nicotine with metallic ions and to promote the absorption of nicotine through the lining of the oral cavity of the individual,
    said first spray container being utilized by the individual for a selected period of time to administer said first liquid carrier solution to the oral cavity of the individual, after which said second spray container is utilized for a selected period of time to administer said second liquid carrier solution to the oral cavity of the individual.

4. The apparatus of claim 3 wherein each of said liquid carrier solutions includes
    (a) less than 2% by weight nicotine;
    (b) less than 10% by weight of at least one stimulant; and,
    (c) less than 250 ppm of a sequestering agent which binds with metallic ions and acids.

5. A composition for facilitating the absorption of nicotine through the linings of the oral cavity of an individual, comprising a liquid carrier solution including
    (a) a liquid carrier;
    (b) less than 2% by weight of nicotine;
    (c) less than 10% by weight of at least one stimulant; and,
    (d) less than 250 ppm of a sequestering agent which binds with metallic ions and acids to reduce the likelihood said nicotine will bind with said metallic ions and acids to impede absorption of said nicotine through the lining of the oral cavity of an individual, said stimulant, said nicotine, and said sequestering agent being admixed together with said liquid carrier to form said liquid carrier solution.

* * * * *